United States Patent
Gstrein et al.

(10) Patent No.: US 7,208,327 B2
(45) Date of Patent: Apr. 24, 2007

(54) METAL OXIDE SENSORS AND METHOD OF FORMING

(75) Inventors: Florian Gstrein, Portland, OR (US); Valery M. Dubin, Portland, OR (US)

(73) Assignee: Intel Corporation, Santa Clara, CA (US)

( * ) Notice: Subject to any disclaimer, the term of this patent is extended or adjusted under 35 U.S.C. 154(b) by 86 days.

(21) Appl. No.: 11/136,585

(22) Filed: May 25, 2005

(65) Prior Publication Data

US 2006/0267051 A1    Nov. 30, 2006

(51) Int. Cl.
*H01L 29/06*  (2006.01)
*H01L 31/072* (2006.01)
*H01L 31/109* (2006.01)
*H01L 31/0328* (2006.01)
*H01L 31/0336* (2006.01)

(52) U.S. Cl. .......................................... 438/10; 438/17
(58) Field of Classification Search ............... 438/3–17
See application file for complete search history.

(56) References Cited

U.S. PATENT DOCUMENTS 6,838,297 B2 * 1/2005 Iwasaki et al. ............... 438/20
2006/0234396 A1 * 10/2006 Tomita et al. ................ 438/3

OTHER PUBLICATIONS

Keat Ghee Ong et al.; A Wireless, Passive Carbon Nanotube-Based Gas Sensor, IEEE Sensors Journal, vol. 2, No. 2, Apr. 2002; pp. 82-88.

Niloy Mukherjee et al.; "Fabrication of nanoporous tungsten oxide by galvanostatic anodization;" J. Mater. Res., vol. 18, No. 10, Oct. 2003 pp. 2296-2299.

G.K. Mor et al.; "Fabrication of tapered, conical-shaped titania nanotubes;" J. Mater. Res., vol. 18, No. 11, Nov. 2003; pp. 2588-2593.

Junya Suehiro et al.; "Fabrication of a carbon nanotube-based gas sensor using dielectrophoresis and its application for ammonia detection by impedance spectroscopy;" J. Phys. D: Appl. Phys. 36 (2003) pp. L109-L114.

Oomman K. Vargese et al.; "A Titania Nanotube-Array Room-Temperature Sensor for Selective Detection of Hydrogen at Low Concentrations;" Journal of Nanoscience and Nanotechnology; 2004., vol. 4, No. 7; pp. 733-737.

* cited by examiner

*Primary Examiner*—Cuong Nguyen
(74) *Attorney, Agent, or Firm*—Fleshner & Kim, LLP

(57) ABSTRACT

A metal oxide sensor is provided on a semiconductor substrate to provide on-chip sensing of gases. The sensor may include a metal layer that may have pores formed by lithography to be of a certain width. The top metal layer may be oxidized resulting in a narrowing of the pores. Another metal layer may be formed over the oxidized layer and electrical contacts may be formed on the metal layer. The contacts may be coupled to a monitoring system that receives electrical signals indicative of gases sensed by the metal oxide sensor.

13 Claims, 7 Drawing Sheets

METAL OXIDE SENSORS AND METHOD OF FORMING

FIELD

Embodiments of the present invention may relate to gas sensors. More particularly, embodiments of the present invention may relate to the formation of metal oxide semiconductor (MOS) sensors.

BACKGROUND

Gas sensors are used in many industrial, medical and commercial applications. For example, oxygen sensors are used in the monitoring of combustion engine environments to increase engine performance and reduce emission of green house gases. Ammonia sensors may be important for monitoring ambient ammonia concentrations related to many environmental issues such as acidification, human health and climate change through particle formation. Carbon dioxide sensors may also be widely used in food and medicine packages as a means of detecting spoilage. Additionally, gas sensors for chip-based applications may detect gas levels of effluents such as $H_{2,(g)}$, $NO_{x,(g)}$, $CO_{(g)}$, $H_2S_{(g)}$, chemical weapons, petrochemical products, alcohols, etc. for applications such as manufacture process monitoring, homeland security, health monitoring, and disease detection.

BRIEF DESCRIPTION OF THE DRAWINGS

The foregoing and a better understanding of the present invention may become apparent from the following detailed description of arrangements and example embodiments and the claims when read in connection with the accompanying drawings, all forming a part of the disclosure of this invention. While the foregoing and following written and illustrated disclosure focuses on disclosing arrangements and example embodiments of the invention, it should be clearly understood that the same is by way of illustration and example only and embodiments of the present invention are not limited thereto.

The following represents brief descriptions of the drawings in which like reference numerals represent like elements and wherein.

DETAILED DESCRIPTION

Figure 1:
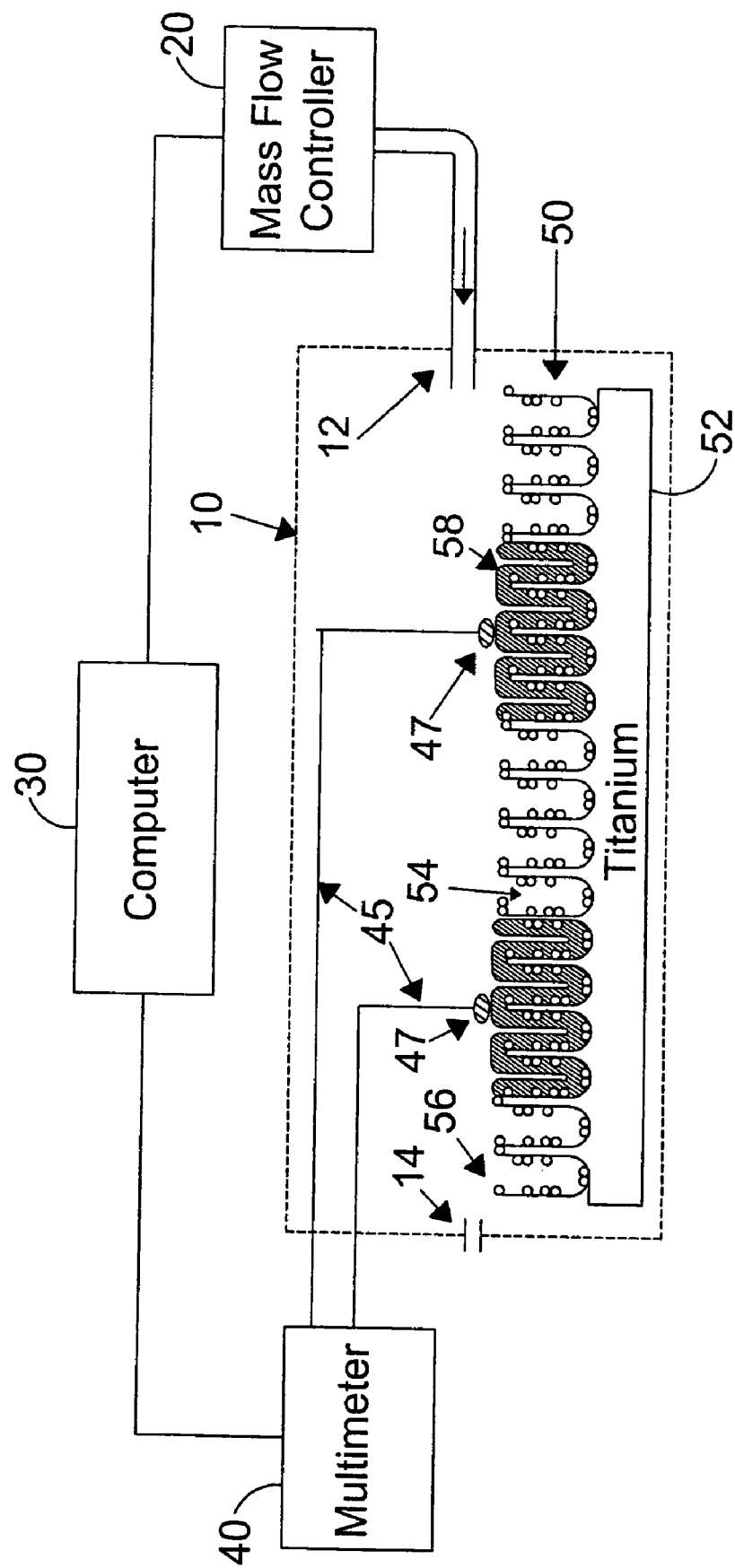
FIG. 1 is a diagram of a gas sensor according to an example arrangement.

In the following detailed description, like reference numerals and characters may be used to designate identical, corresponding or similar components in differing figure drawings. Further, in the detailed description to follow, example sizes/models/values/ranges may be given although the present invention is not limited to the same. Where specific details are set forth in order to describe example embodiments of the invention, it should be apparent to one skilled in the art that embodiments of the present invention can be practiced without these specific details.

Embodiments of the present invention may provide a non-disruptive integrated and controlled scaling of gas sensors in a CMOS-compatible process flow. Nanostructures may be optimized for individual sensing applications. That is, nanostructures may be specifically tailored for detection speed and detection accuracy. The nanostructures may also be optimized for sensing of specific gas levels (i.e., low versus high levels and relative changes of high gas levels). Additionally, embodiments of the present invention may be integrated into a CMOS process flow to allow on-chip electrical detection and sensor registration.

FIG. 1 is a diagram of a gas sensor according to an example arrangement. Other arrangements are also possible. More specifically, FIG. 1 shows a test chamber 10 that houses a semiconductor gas sensor 50. The test chamber 10 is coupled to a mass flow controller 20 that regulates an amount of gas to enter the chamber 10. The controller 20 may be controlled by a computer system 30 (or other type of monitoring device/system). A multimeter 40 may be coupled to the gas sensor 50 within the test chamber 10 by way of copper leads 45 or other type of electrical leads. The multimeter 40 may provide output signals indicative of the sensed readings to the computer system 30. Gas may flow into the chamber 10 by way of an inlet port 12 and flow out of the chamber 10 by way of an outlet port 14. The computer controlled multimeter 40 and mass flow controller 20 may be used to measure the resistance of the sensor 50 (and adjust the gas flow if desired).

The gas sensor 50 according to the example arrangement shown in FIG. 1 will now be described. The gas sensor 50 may include a titanium (Ti) substrate 52 on which titania nanotubes 54 are formed. The nanotubes 54 may be fabricated in this arrangement by anodizing a titanium foil in an electrolyte solution including acetic acid and hydrofluoric acid in water. An anodization potential of 10 volts may be used, for example. The anodized sample may be amorphous and crystallization may be achieved by annealing. The annealed samples may be coated with a palladium layer 56 having a thickness of about 10 nm deposited by thermal evaporation. Contacts 58 such as platinum electrodes (e.g., 40 nm thick and 2.0 mm in diameter) may then be sputter-coated onto the sample. The copper leads 45 may be attached to the contacts 58 by contacts 47 such as silver epoxy, for example.

The gas sensor 50 shown in FIG. 1 may be formed by electrochemical anodization, which may rely on a field-induced dissolution of Ti metal foils in oxalic acid and hydrofluoric acid, respectively. In addition to the electrochemical anodization of the metal films, the metal oxides (formed from the Ti) may also be prepared by sol-gel techniques, colloidal chemistry, physical vapor deposition (PVD), and chemical vapor deposition (CVD) methods. These methods (such as the sol-gel technique) may not be fully compatible with semiconductor process flow (i.e., the fab process). These methods also may not be easily scaled for high volume manufacturing and may only provide limited process control over the nanostructure that results in devices having irreproducible sensing properties. The pores sizes may also be limited to 30 nm for the $TiO_2$ layer. Additionally, electrochemical oxidation may be difficult to control.

The above described gas sensor 50 may be similarly formed by using a tungsten (W) substrate. However, for tungsten gas sensors formed in a similar manner, the pore sizes may be limited to 20 nm within the WO3 layer.

Embodiments of the present invention may define nanostructures (such as pores, tubes and/or wires/pillars) by lithographic patterning and reactive ion etching. This may involve using fluorinated etch gases such as $SF_6^+$, $CF_4^+$, $XeF_2^+$, $XeF_4^+$, for example, for unidirectional etching of W and/or Ti. With these lithographic techniques, nanostructures can easily be defined and etched including for diameters of approximately 100 nm. While the following example discusses W and Ti, other metals may also be used including, but not limited to nickel (Ni), tin (Sn), zinc (Zn), tantalum (Ta) and molybdenum (Mo). These other metals of Ni, Sn, Zn, Ta and Mo may be oxidized and etched similarly to W and Ti. Embodiments of the present invention also include at least these metals.

Figure 2A:
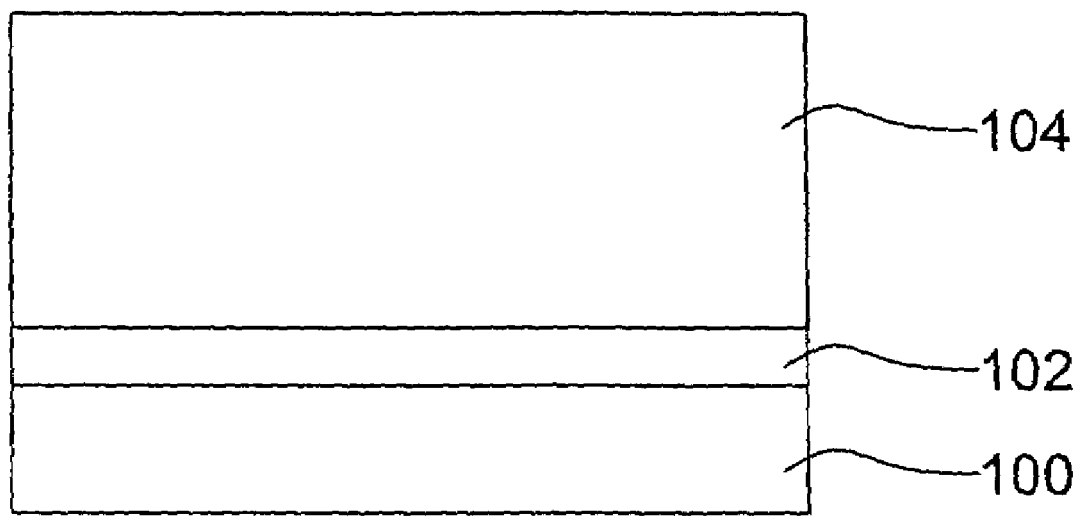
FIGS. 2A–2E show side views of a gas sensor during a fabrication process according to an example embodiment of the present invention.

FIGS. 2A–2E show side views of a gas sensor during a fabrication process according to an example embodiment of the present invention. Other embodiments and configurations are also within the scope of the present invention. More specifically, FIG. 2A shows a silicon (Si) substrate 100 is initially provided. The silicon substrate 100 may be oxidized to form an oxidized layer 102 over the silicon substrate 100. A W or Ti layer 104 may then be formed over the oxidized layer 102 using a physical vapor deposition (PVD) method or other type of method (such as thermal evaporation, chemical vapor deposition (CVD), etc.).

Figure 2B:
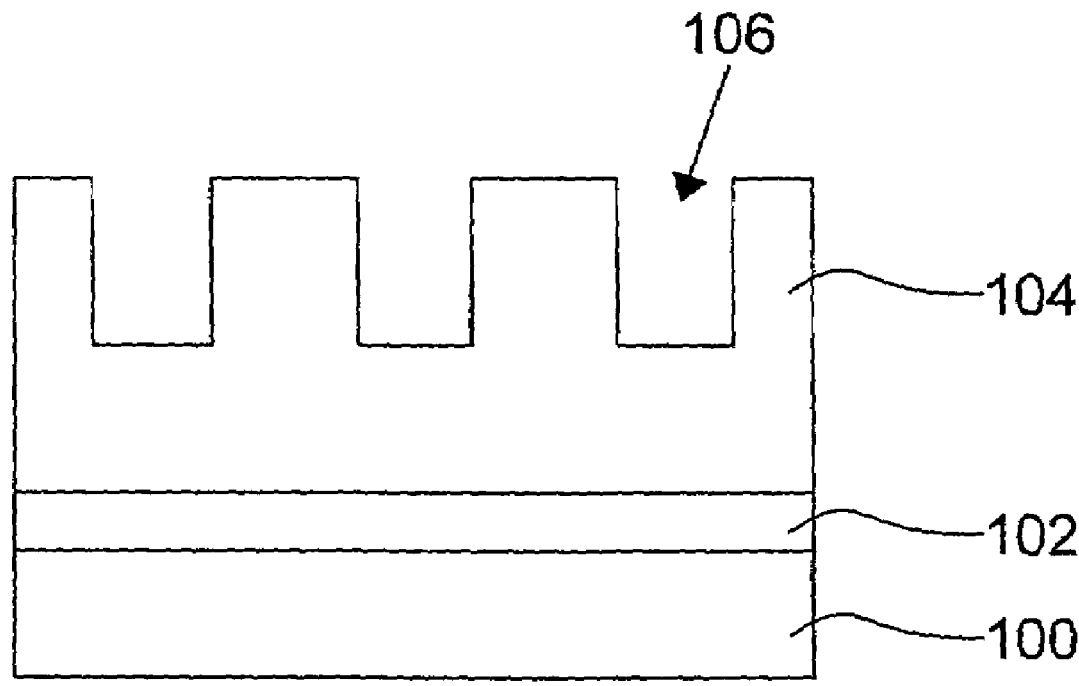

FIG. 2B shows nanostructures (or pores) 106 formed in the W or Ti layer 104 by lithography and etching. The lithography may define the nanostructures to have a width of approximately 60 nm–500 nm, for example. Even more specifically, the nanostructures may have a width of approximately 10–200 nm. The etching may be performed with fluorinated etch gases such as $SF_6^+$, $CF_4^+$, $XeF_2^+$, $XeF_4^+$, for example.

Figure 2C:
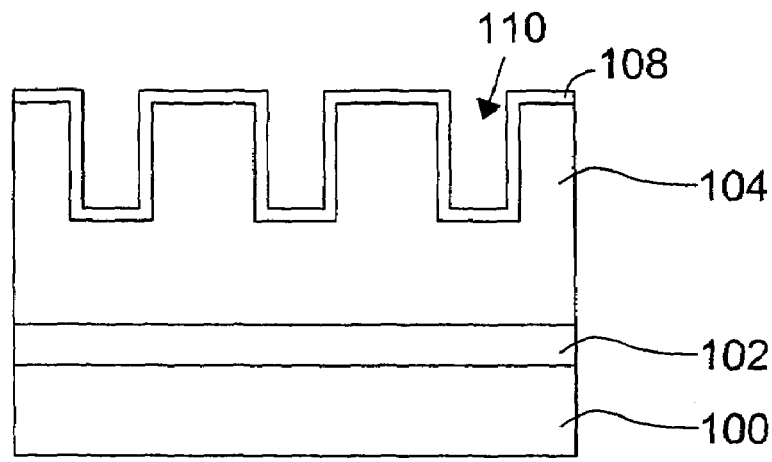
Figure 2D:
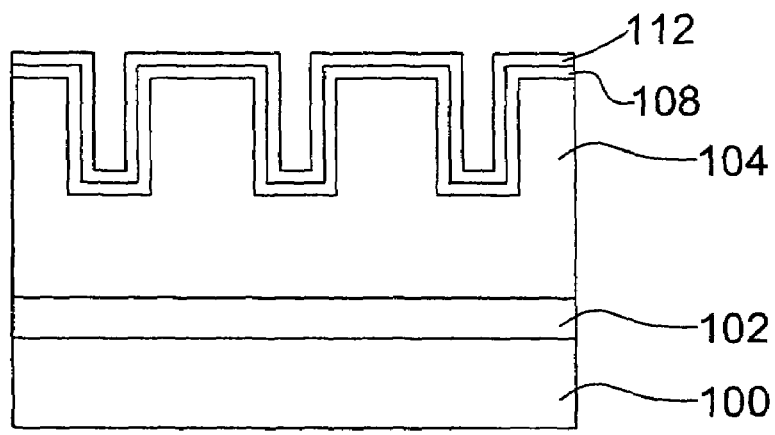
Figure 2E:
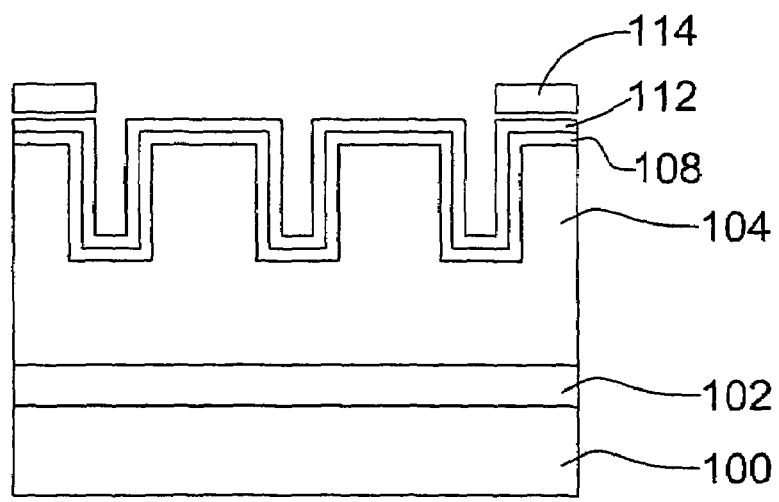

FIG. 2C shows the structure after a controlled oxidation of the W or Ti layer to form a $WO_3$ or $TiO_2$ layer 108. This results in narrowed nanostructures 110 (or narrowed pores). FIG. 2D shows a palladium layer 112 formed over the $WO_3$ or $TiO_2$ layer 108. The palladium layer 112 (or metal layer) may be provided by any of a number of plating techniques and may correspond to the contacts 58 shown in FIG. 1. This may form a Schottky contact. FIG. 2E shows the formation of contacts 114 over the palladium layer 112. The contacts 114 may correspond to the contacts 47 shown in FIG. 1. These contacts 114 may be coupled by electrical leads/contacts (such as copper leads) to a monitoring device (such as the multimeter 40 shown in FIG. 7). The gas sensor shown in FIG. 2E may be provided within a testing chamber 10 such as shown in FIG. 1 or may be provided within any other type of semiconductor environment in order to provide sensing of gases. That is, the gas sensor may communicate by signals across electrical leads/contacts to a monitoring system.

As discussed above, rather than using W or Ti to form a metal layer, embodiments of the present invention may use other metals such as Ni, Sn, Zn, Ta and Mo. These metal layers may similarly be used to form metal oxide semiconductor layers such as nickel oxide, tin oxide, zinc oxide, tantalum oxide and molybdenum oxide.

Rather than palladium or platinum, example embodiments of the present invention may also use/deposit other metals with suitable work functions (i.e., within a band gap of the metal oxide semiconductor) over the metal oxide layer. Any known method of deposition may be used.

Figure 3:
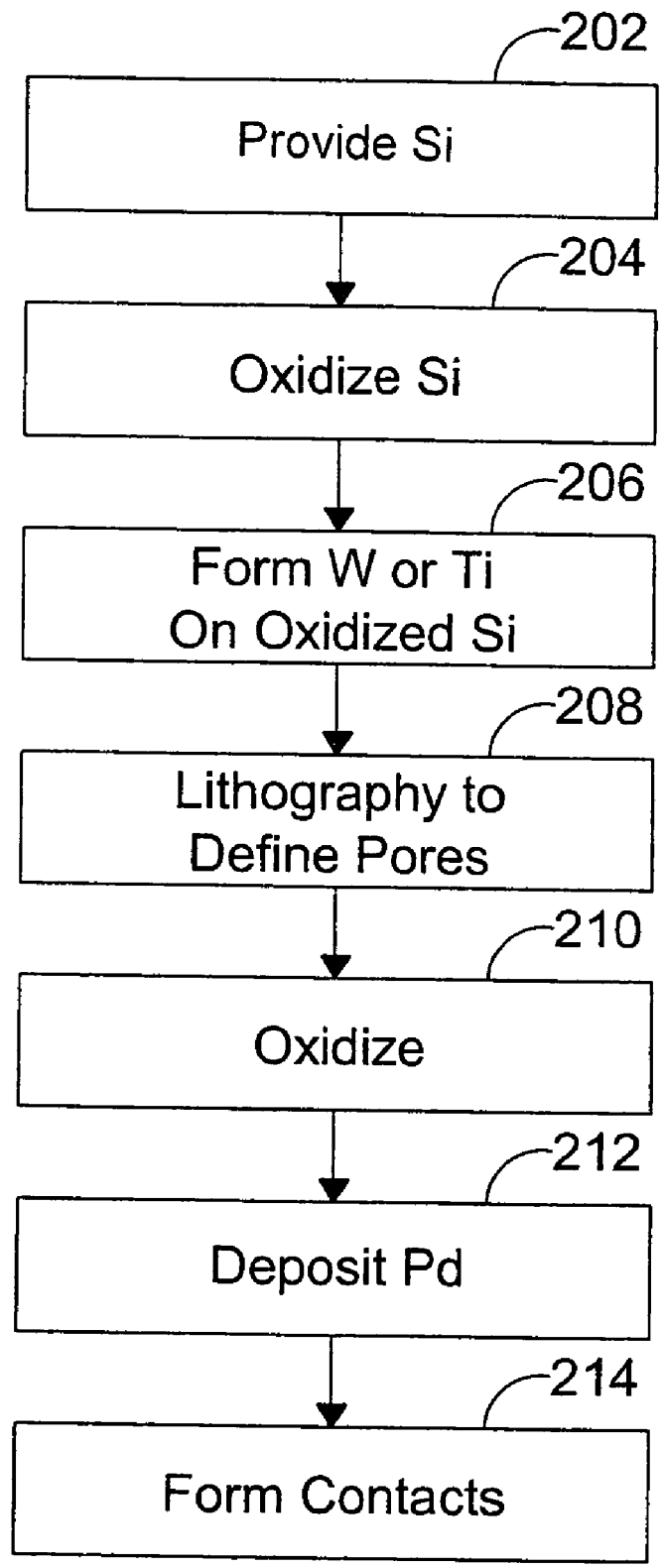
FIG. 3 is a flow chart showing operations according to an example embodiment of the present invention.

FIG. 3 is a flow chart showing operations according to an example embodiment of the present invention. Other embodiments, operations and orders of operation are also within the scope of the present invention. More specifically, a silicon (Si) layer may be provided in block 202. The silicon layer may be oxidized in block 204. In block 206, tungsten (W) or titanium (Ti) may be formed on the oxidized Si. Lithography and/or etching may then be used in block 208 to define nanostructures (such as pores or tubes) within the W or Ti. The top surface of W or Ti may be oxidized in block 210 to form one of the metal oxides $WO_3$ or $TiO_2$. The oxidation may result in a narrowing of the nanostructures (or pores). A palladium (Pd) layer may then be deposited in block 212 using any of a number of known plating methods. Subsequently in block 214, the contacts may be formed.

The metal oxide semiconductors ($WO_3$, $TiO_2$) may be formed by a temperature-controlled oxidation. The oxidation may lead to a further narrowing of the nanostructures (or pores) of the lithographically-defined W and Ti thin films. As one example, for every 10 nm of W that are consumed during oxidation, approximately 15 nm of $WO_3$ may evolve. Accordingly, this may result in a significant narrowing of the initial 100 nm wide W nanostructures down to approximately 20–50 nm wide nanostructures. Again, other metal oxide semiconductors besides $WO_3$ and $T_iO_2$ such as nickel oxide, tin oxide, zinc oxide, tantalum oxide and molybdenum oxide may also be used in other example embodiments of the present invention.

The parent metal and metal oxide may also form ohmic contacts. For example, Schottky contacts may be formed by electroless plating of a variety of transition metals with work functions that are more positive than a conduction band edge of the metal oxide semiconductor. The resistance of the contacts may depend on the gas concentration because the work function of metals supported on the metal oxide semiconductor may change following gas adsorption and in turn may result in a change of a barrier height of the metal/metal oxide Schottky contact. The barrier height change may also affect the current-voltage characteristics. Gas adsorption may also result in lower barrier heights that in turn results in a significant lowering on the low-bias resistance of the Schottky contact. A large range of transition metals, such as but not limited to, palladium (Pd) and platinum (Pt) can be electrolessly plated into the nanostructures (i.e., pores). Other metal layers having suitable work functions may also be used. As discussed above, embodiments of the present invention may readily integrate the process flow into a CMOS process flow to provide on-wafer read out and sensor registration.

Figure 4:
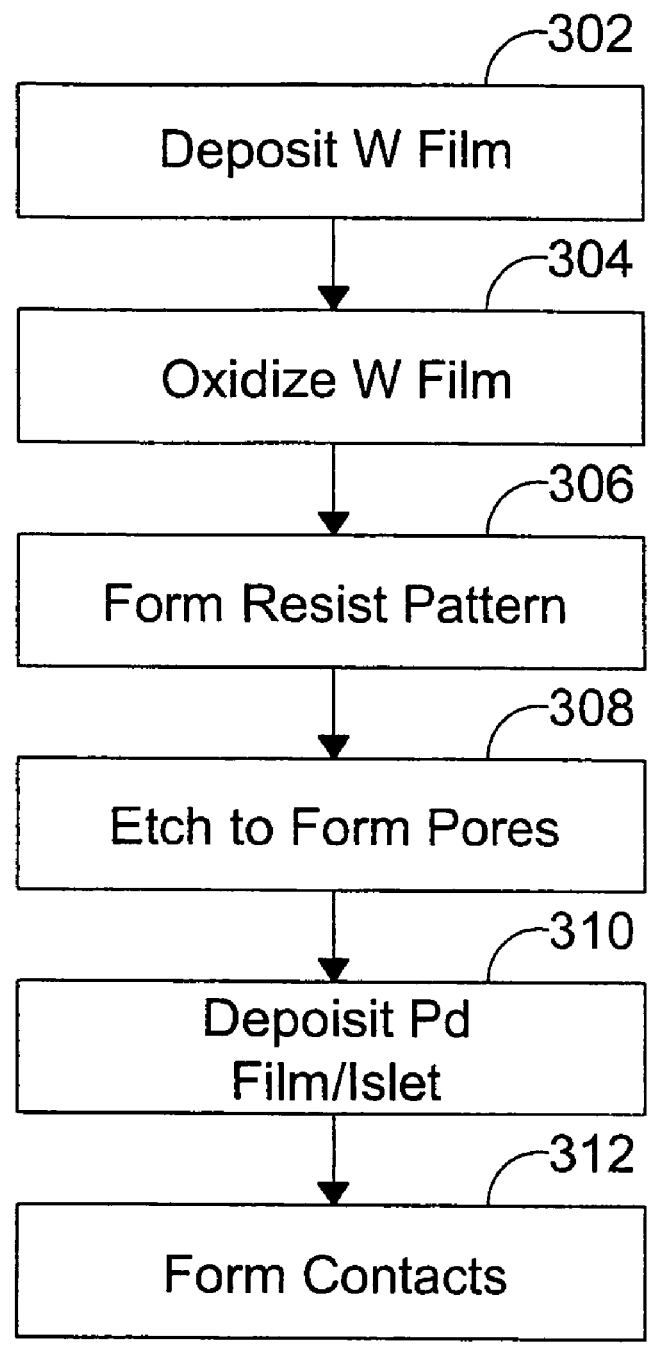
FIG. 4 is a flow chart showing operations according to an example embodiment of the present invention.

FIG. 4 is a flow chart showing operations according to an example embodiment of the present invention. Other embodiments, operations and orders of operation are also within the scope of the present invention. More specifically, FIG. 4 shows that a W film (or layer) may be deposited on silicon in block 302. The W film may be deposited by PVD methods, for example. The W film may have a thickness of approximately 10 nm–10 μm, for example. In block 304, the W film may be oxidized to form $WO_3$. This may be performed in oxygen gas ($O_2$), for example, at a temperature between approximately 200° C. and 400° C. for anywhere from approximately 10 minutes to 4 hours. In block 306, a resist pattern is formed on the $WO_3$ layer and the $WO_3$ layer may be etched in block 308 through the resist pattern to form nanostructures (such as pores) in the $WO_3$ layer. These pores may be in a range of approximately 5 nm to 1 μm. Palladium (Pd) film/islets may be deposited on the oxidized surface by electroless plating, CVD, PVD, etc. in block 310. Other embodiments of the present invention may also deposit other metal films/islets. A detailed discussion involving these other metals will be omitted for ease of illustration. The palladium film/islets may have a width of less than approximately 50 nm, for example. The palladium may modify a band gap structure of the semiconducting oxide (i.e., the $WO_3$ layer) and may make it responsive to hydrogen adsorption. Other sensitizers may also be used, including gold (Au), doping oxide with transition metals, carbon, nitrogen, etc. In block 312, contacts may also be formed by a deposition of platinum (Pt), aluminum (Al), palladium (Pd), nickel (Ni), cobalt (Co), etc. on the surface of the porous structure. Hard masks may be used for patterning of the pores, contacts, etc. Additionally, the conductivity of the semiconducting metal oxide ($WO_3$) may be changed between contacts with the adsorption of hydrogen.

Figure 5:
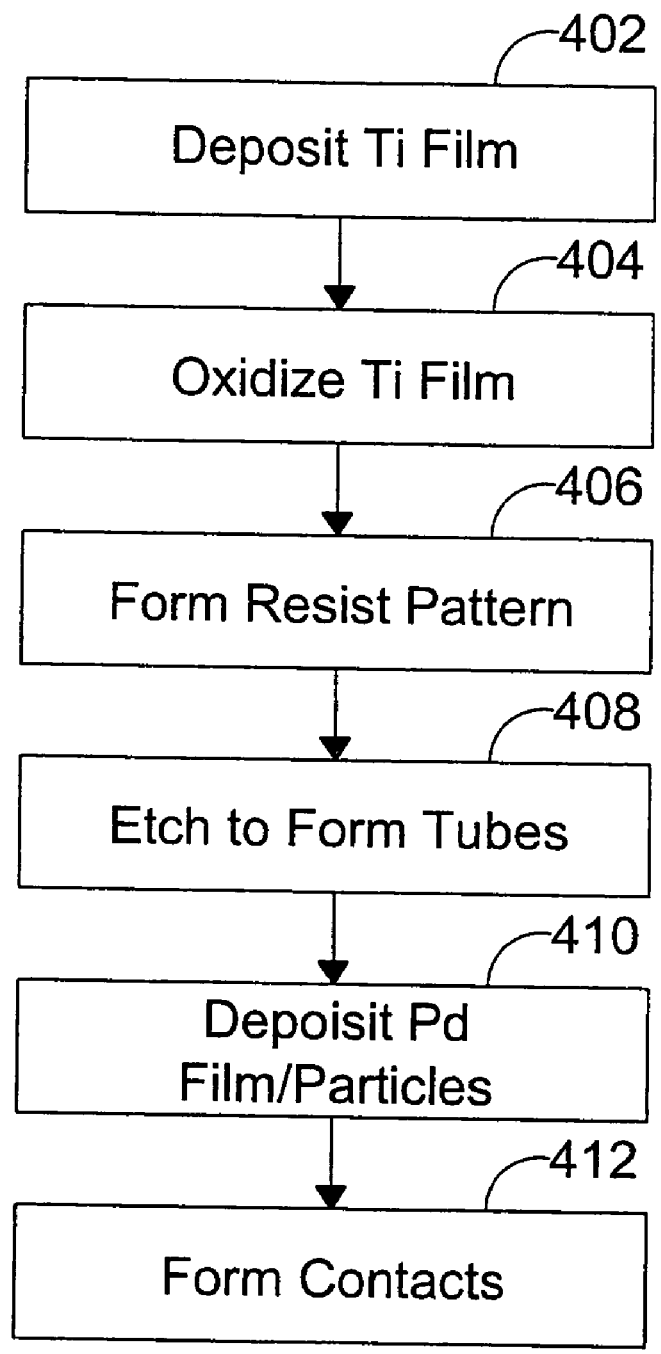
FIG. 5 is a flow chart showing operations according to an example embodiment of the present invention.

FIG. 5 is a flow chart showing operations according to an example embodiment of the present invention. Other embodiments, operations and orders of operation are also within the scope of the present invention. More specifically, FIG. 5 shows that a titanium (Ti) film (or layer) is deposited in block 402. The Ti film may be deposited by PVD methods, for example. The Ti film may have a thickness of approximately 10 nm–10 μm. In block 404, the Ti film may be oxidized to form $TiO_2$. This may be performed in oxygen gas ($O_2$), for example, at a temperature between approximately 200° C. and 400° C. for anywhere from approximately 10 minutes to 4 hours. In block 406, a resist pattern is formed on the $TiO_2$ layer and the $TiO_2$ layer may be etched in block 408 through the resist pattern to form nanostructures (such as tubes) in the $TiO_2$ layer. These tubes may have an inner diameter in a range of approximately 5 nm to 500 nm. Alternatively, a hard mask may be used for patterning. Palladium (Pd) film/particles may be deposited on the oxidized surface by electroless plating, CVD, PVD, etc. in block 410. In block 412, contacts may also be formed by a deposition of platinum (Pt), aluminum (Al), palladium (Pd), nickel (Ni), cobalt (Co), etc. on the surface of the porous structure. Hard masks may be used for patterning of the pores, contacts etc. Titania tubes may also be formed by oxidation of patterned titanium.

Embodiments of the present invention may integrate the formation of metal oxide gas sensors into a high-volume semiconductor process flow using non-disruptive and CMOS compatible techniques. Additionally, gas sensors may be fabricated with highly reproducible performance due to tight process control over nanostructures (i.e., pore size, pore size distribution, metal oxide thickness, nanotubes/nanowires diameters and lengths). Embodiments of the present invention may utilize CMOS technology to enable on-chip amplification of an electrical signal as well as register individual sensor elements on the die with nanostructures optimized for particular sensing tasks.

Embodiments of the present invention may have uniform and tightly controlled nanostructures. The nanostructures may be optimized for individual sensing applications such as nanostructure detection speed and detection accuracy.

While embodiments have been described with respect to a silicon substrate and the deposition of a W or Ti film, other films may also be deposited such as zinc (Zn) or nickel (Ni). Other films are also possible.

Figure 6:
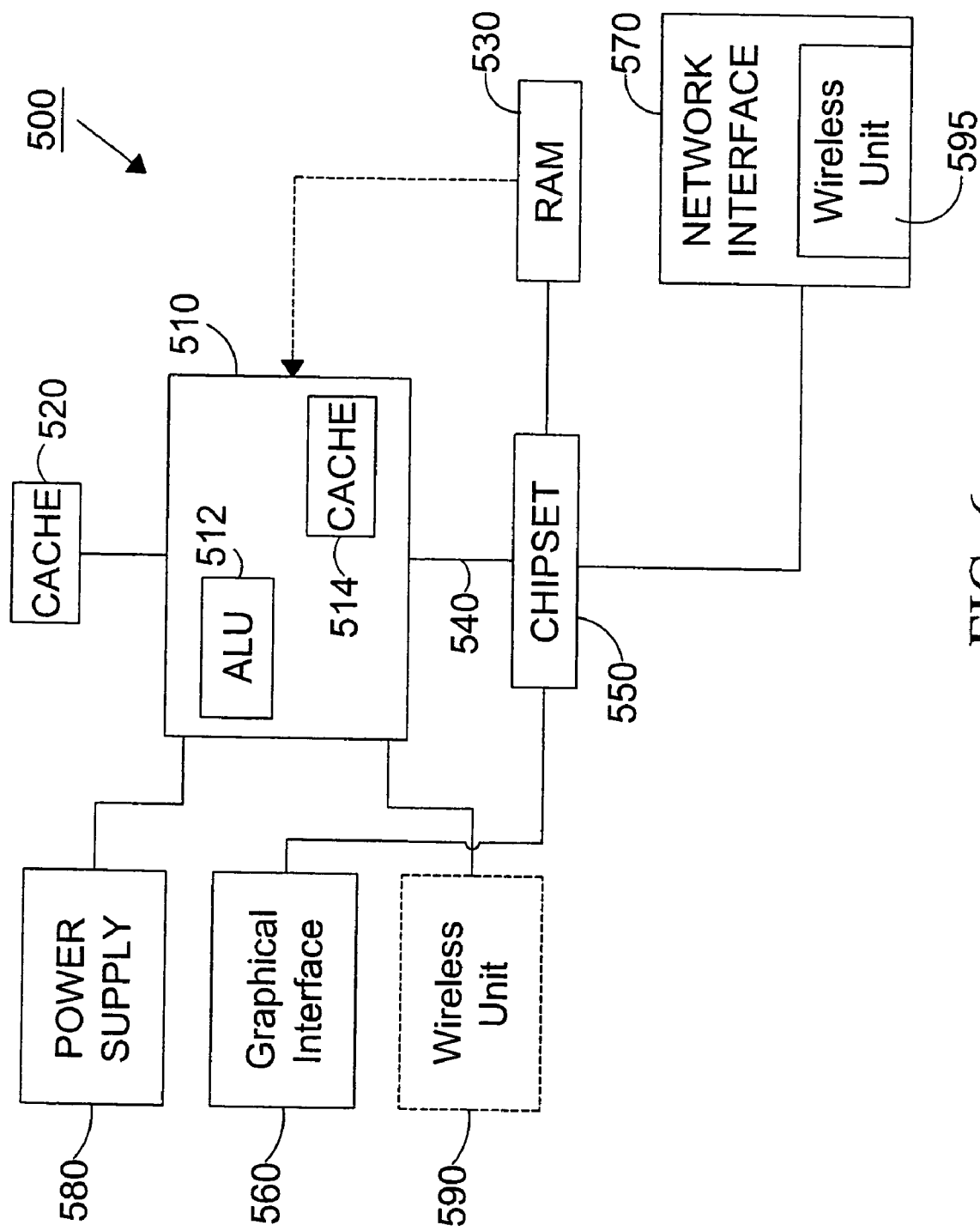
FIG. 6 is a block diagram of a system that may include a gas sensor according to an example embodiment of the present invention.

FIG. 6 is a block diagram of a system (such as a computer system 500) that may include a gas sensor according to an example embodiment of the present invention. Other embodiments and configurations are also within the scope of the present invention. More specifically, the computer system 500 may include a processor 510 that may have many sub-blocks such as an arithmetic logic unit (ALU) 512 and an on-die (or internal) cache 514. The processor 510 may also communicate to other levels of cache, such as off-die cache 520. Higher memory hierarchy levels such as a system memory (or RAM) 530 may be accessed via a host bus 540 and a chip set 550. The system memory 530 may also be accessed in other ways, such as directly from the processor 510 and/or without passing through the host bus 540 and/or the chip set 550. In addition, other off-die functional units such as a graphics interface 560 and a network interface 570, to name just a few, may communicate with the processor 510 via appropriate busses or ports. The processor 510 may also be powered by an external power supply 580. The system may also include a wireless interface 590 or 595 to interface the system 500 with other systems, networks, and/or devices via a wireless connection. A die or chip containing the structure discussed above or manufactured/fabricated as discussed above may be provided anywhere with the system 500 such as within the chip set 550. Additionally, the system may be formed without any buses such as by using point-to-point connections. Still further, the chip set 550 may be provided on the processor 510 rather than be external to the processor 510.

Additionally, a die as discussed above or manufactured/fabricated as discussed above may be provided in any type of sensor to sense specific gas vapors. The die may be coupled to a monitoring device (such as shown in FIG. 1, for example) so as to properly sense voltages/currents from the respective contacts of the gas sensor. These signals would be indicative of sensed gases.

Systems including embodiments of the present invention may be of any type. Examples of represented systems include computers (e.g., desktops, laptops, handhelds, servers, tablets, web appliances, routers, etc.), wireless communications devices (e.g., cellular phones, cordless phones, pagers, personal digital assistants, etc.), computer-related peripherals (e.g., printers, scanners, monitors, etc.), entertainment devices (e.g., televisions, radios, stereos, tape and compact disc players, video cassette recorders, camcorders, digital cameras, MP3 (Motion Picture Experts Group, Audio Layer 3) players, video games, watches, etc.), and the like.

Any reference in this specification to "one embodiment," "an embodiment" "example embodiment," etc., means that a particular feature, structure, or characteristic described in connection with the embodiment is included in at least one embodiment of the invention. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments. Further, certain method procedures may have been delineated as separate procedures; however, these separately delineated procedures should not be construed as necessary order dependent in their performance. That is, some procedures may be able to be performed in an alternative ordering, simultaneously, etc.

Although embodiments of the present invention have been described with reference to a number of illustrative embodiments thereof, it should be understood that numerous other modifications and embodiments can be devised by those skilled in the art that will fall within the spirit and scope of the principles of this invention. More particularly, reasonable variations and modifications are possible in the component parts and/or arrangements of the subject combination arrangement within the scope of the foregoing disclosure, the drawings and the appended claims without departing from the spirit of the invention. In addition to variations and modifications in the component parts and/or arrangements, alternative uses will also be apparent to those skilled in the art.

What is claimed is:

1. A method of forming a metal oxide sensor comprising:
   depositing a metal layer on a semiconductor substrate;
   forming nanostructures within the metal layer;
   oxidizing the metal layer to form a metal oxide semiconductor;
   depositing a metallic layer on the metal oxide semiconductor; and
   forming gas sensor contacts on the deposited metallic layer.

2. The method of claim 1, wherein forming the nanostructures comprises using lithography and etching to form the nanostructures.

3. The method of claim 1, wherein the nanostructures comprise pores.

4. The method of claim 1, wherein the nanostructures comprise tubes.

5. The method of claim 1, wherein the nanostructures have a width of approximately 10–200 nm.

6. The method of claim 1, wherein depositing the metallic layer comprises providing a metal layer using a plating technique.

7. The method of claim 1, wherein the metal layer deposited on the semiconductor substrate comprises one of tungsten, titanium, nickel, tin, zinc, tantalum and molybdenum.

8. The method of claim 1, further comprising forming an oxidized layer over the semiconductor substrate prior to depositing the metal layer.

9. The method of claim 1, further comprising attaching electric leads to the contacts.

10. The method of claim 9, further comprising sensing gas vapors using the metal oxide sensor having the gas sensor contacts.

11. A method comprising:
    depositing a metal layer;
    lithographically forming nanostructures within the metal layer;
    forming a metal oxide semiconductor on the metal layer;
    depositing a metallic layer on the metal oxide semiconductor; and
    forming electrical contacts on the metallic layer.

12. The method of claim 11, wherein the metal layer comprises one of tungsten, titanium, nickel, tin, zinc, tantalum and molybdenum.

13. The method of claim 11, further comprising monitoring gas vapors based on signals received from the electrical contacts.

* * * * *